(12) United States Patent
Hsu et al.

(10) Patent No.: US 11,819,604 B2
(45) Date of Patent: Nov. 21, 2023

(54) BREATHING AIRFLOW DETECTING DEVICE FOR A NEBULIZING DEVICE

(71) Applicant: PU YUAN BIOTECH CO., LTD., Taipei (TW)

(72) Inventors: Hung Kuang Hsu, Taipei (TW); Shih Ming Chuang, Taipei (TW); Yu Chih Chen, Taipei (TW)

(73) Assignee: Pu Yuan Biotech Co., Ltd., Taipei (TW)

( * ) Notice: Subject to any disclaimer, the term of this patent is extended or adjusted under 35 U.S.C. 154(b) by 868 days.

(21) Appl. No.: 16/868,794

(22) Filed: May 7, 2020

(65) Prior Publication Data

US 2021/0299366 A1 Sep. 30, 2021

(30) Foreign Application Priority Data

Mar. 31, 2020 (TW) .................................. 109111069

(51) Int. Cl.
*A61M 11/04* (2006.01)

(52) U.S. Cl.
CPC ..... *A61M 11/04* (2013.01); *A61M 2205/3306* (2013.01); *A61M 2230/42* (2013.01)

(58) Field of Classification Search
CPC ........... A61M 11/04; A61M 2205/3306; G01L 11/02; G01L 23/06
See application file for complete search history.

(56) References Cited

U.S. PATENT DOCUMENTS

| | | | | |
|---|---|---|---|---|
| 5,376,785 A | * | 12/1994 | Chin | G01D 5/34 250/227.21 |
| 6,427,682 B1 | * | 8/2002 | Klimowicz | A61M 15/025 128/200.14 |
| 2014/0190496 A1 | * | 7/2014 | Wensley | A61M 11/042 131/273 |
| 2022/0110583 A1 | * | 4/2022 | Wallach | A61B 5/486 |

* cited by examiner

*Primary Examiner* — Rachel T Sippel
(74) *Attorney, Agent, or Firm* — Rosenberg, Klein & Lee (57) ABSTRACT

A breathing airflow detecting device for a nebulizing device is disclosed. The breathing airflow detecting device includes a case, wherein a light switching module and a light blocking element are arranged in the case. The light blocking element is arranged between optical routes of a light emitting element and a light receiving element. When airflow from an inlet blows and swings the light blocking element, the light blocking element blocks light or passes light to the light receiving element. When the light receiving element detects the variation of light, the light receiving element emits a signal from the output port of the light switching module to drive or stop driving a nebulizing device. As a result, when a patient breathes, the nebulizing device is driven such that the volume of the nebulized medicine is accurately inhaled into the patient's lungs.

8 Claims, 9 Drawing Sheets

BREATHING AIRFLOW DETECTING DEVICE FOR A NEBULIZING DEVICE

This application claims priority for Taiwan (R.O.C.) patent application no. 109111069 filed on 31 Mar. 2020, the content of which is incorporated by reference in its entirety.

BACKGROUND OF THE INVENTION

Field of the Invention

The present invention relates to the airflow detecting technology, particularly to a breathing airflow detecting device for a nebulizing device.

Description of the Related Art

For some patients, medicines cannot be swallowed due to the disease, or some medicines need to be inhaled into the lungs by inhalation to achieve curative effects. Therefore, a nebulizing device is required to nebulize the liquid medicines, such that the patient inhales the nebulized medicines. As illustrated in FIG. 1, the patient must wear a mask 20 and inhale the medicines provided by a nebulizing device 24 through a gas tube 26. If a ventilator 30 is supplying oxygen to the patient, the nebulizing device 24 can be installed between the ventilator 30 and the mask 20, oxygen of the ventilator 30 and the medicines of the nebulizing device 24 are delivered to the mask 20, such that the patient inhales oxygen and medicines.

However, when nebulizing the medicines, the lung capacity of inspiratory and expiratory of the patient needs to be considered. Therefore, a great number of medicines are nebulized when the patient inhales airflow whose volume has a fixed range, whereby the medicines are successfully inhaled into the lungs and evenly distributed in each position of the lungs. For example, if the patient inhales in an exaggerated manner such that the airflow is very fast inhaled, the lungs will soon be full of air and inhale the insufficient nebulized medicines, which will degrade the treatment effect.

Therefore, how to detect the airflow to improve the medicine supplying efficiency of the nebulizing device and avoid wasting medicines is an important issue. In the conventional technology, a pressure sensing element is used to sense the wind pressure and then convert it into the volume of airflow. However, the pressure sensing element is expensive. Alternatively, a fan turbine is used to supply medicines, but its structure is complex and difficult to repair when damaged.

To overcome the abovementioned problems, the present invention provides a breathing airflow detecting device for a nebulizing device.

SUMMARY OF THE INVENTION

The primary objective of the present invention is to provide a breathing airflow detecting device for a nebulizing device, which uses a light blocking element to block light emitted by a light switching module. When a patient breathes, the inhaled airflow swings the light blocking element to block the light, thereby generating a signal to drive a nebulizing device. As a result, the nebulized medicines are successfully inhaled into the lungs of the patient to avoid wasting medicines.

Another objective of the present invention is to provide a breathing airflow detecting device for a nebulizing device, which bores the blocking sheet of the light blocking element to form a hole. The light emitted by the light emitting element passes through the hole and reaches the light receiving element. Besides, a blocking edge at one side of the hole can block the light to determine whether sufficient airflow passes through the hole to drive the nebulizing device.

To achieve the abovementioned objectives, the present invention provides a breathing airflow detecting device for a nebulizing device. The breathing airflow detecting device comprises: at least one case with two ends thereof respectively provided with an inlet and an outlet; at least one light switching module, arranged in the at least one case, comprising a light emitting element, a light receiving element, and an output port, wherein the light emitting element is configured to emit light to the light receiving element, and the light receiving element is configured to detect variation of the light; and a light blocking element arranged in the at least one case, wherein when airflow from the inlet blows the light blocking element, the light blocking element swings in a direction vertical to a direction where the light emitting element emits the light, thereby blocking the light or passing the light to the light receiving element; wherein when the light receiving element detects the variation of the light, the light receiving element outputs a signal from the output port to drive or stop driving a nebulizing device.

In an embodiment of the present invention, the at least one case includes a first case and a second case, the second case is embedded into the first case, an end of the second case is provided with the inlet, the first case is provided with the outlet opposite to the inlet, and the airflow flows into the second case and out of the outlet through the inlet, the second case, and the first case.

In an embodiment of the present invention, the second case is provided with a vent, and the airflow coming from the inlet passes through the vent and blows the light blocking element.

In an embodiment of the present invention, the light blocking element is penetrated with a first hole.

In an embodiment of the present invention, a blocking sheet is protruded up from a lower part of the light blocking element in a direction where the light blocking element swings and penetrated with a second hole, and the light passes through the second hole.

In an embodiment of the present invention, the blocking sheet comprises silicone, plastic, or metal.

In an embodiment of the present invention, the light blocking element is a flexible blocking sheet.

In an embodiment of the present invention, the light emitting element, the light receiving element, and the output port are arranged on a bottom board, and the bottom board is arranged on a bottom base.

In an embodiment of the present invention, the inlet of the at least one case is connected to a mask for receiving breathing airflow exhaled by a user.

Below, the embodiments are described in detail in cooperation with the drawings to make easily understood the technical contents, characteristics and accomplishments of the present invention.

BRIEF DESCRIPTION OF THE DRAWINGS

FIG. 1 is a diagram schematically illustrating a user inhaling medicines through a nebulizing device in the conventional technology;

Figure 1:
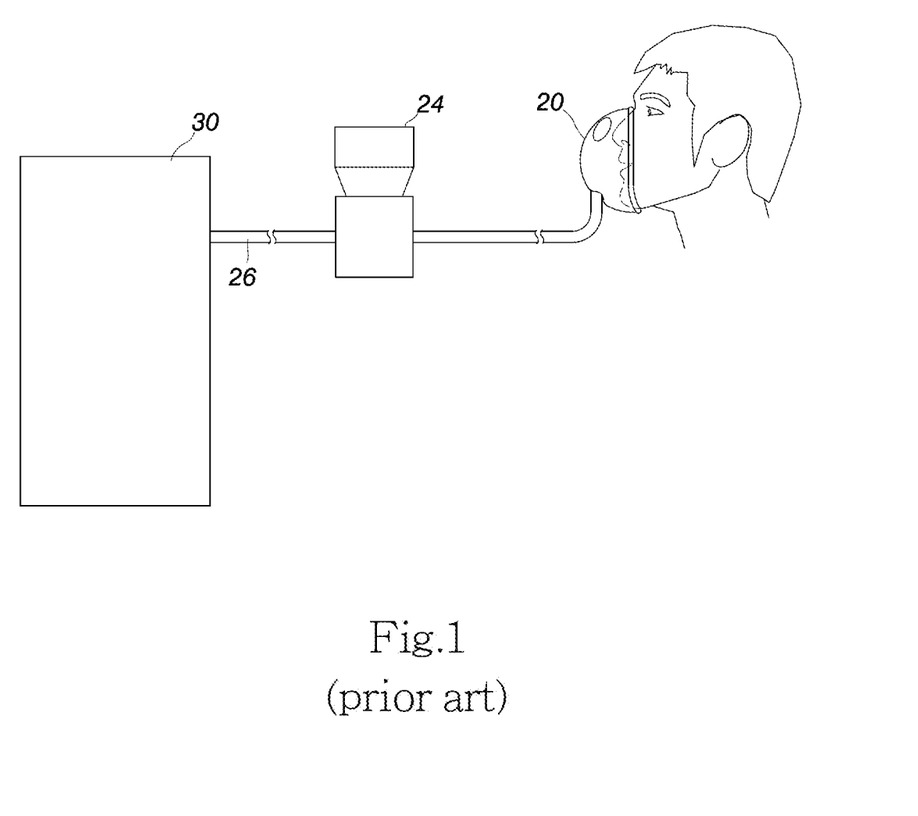
Figure 2A:
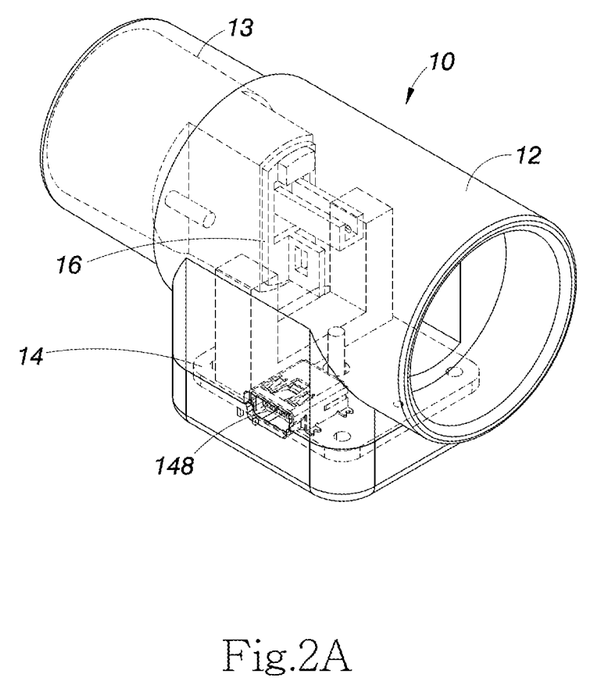
FIG. 2A is a perspective view of a breathing airflow detecting device for a nebulizing device according to an embodiment of the present invention.
Figure 2B:
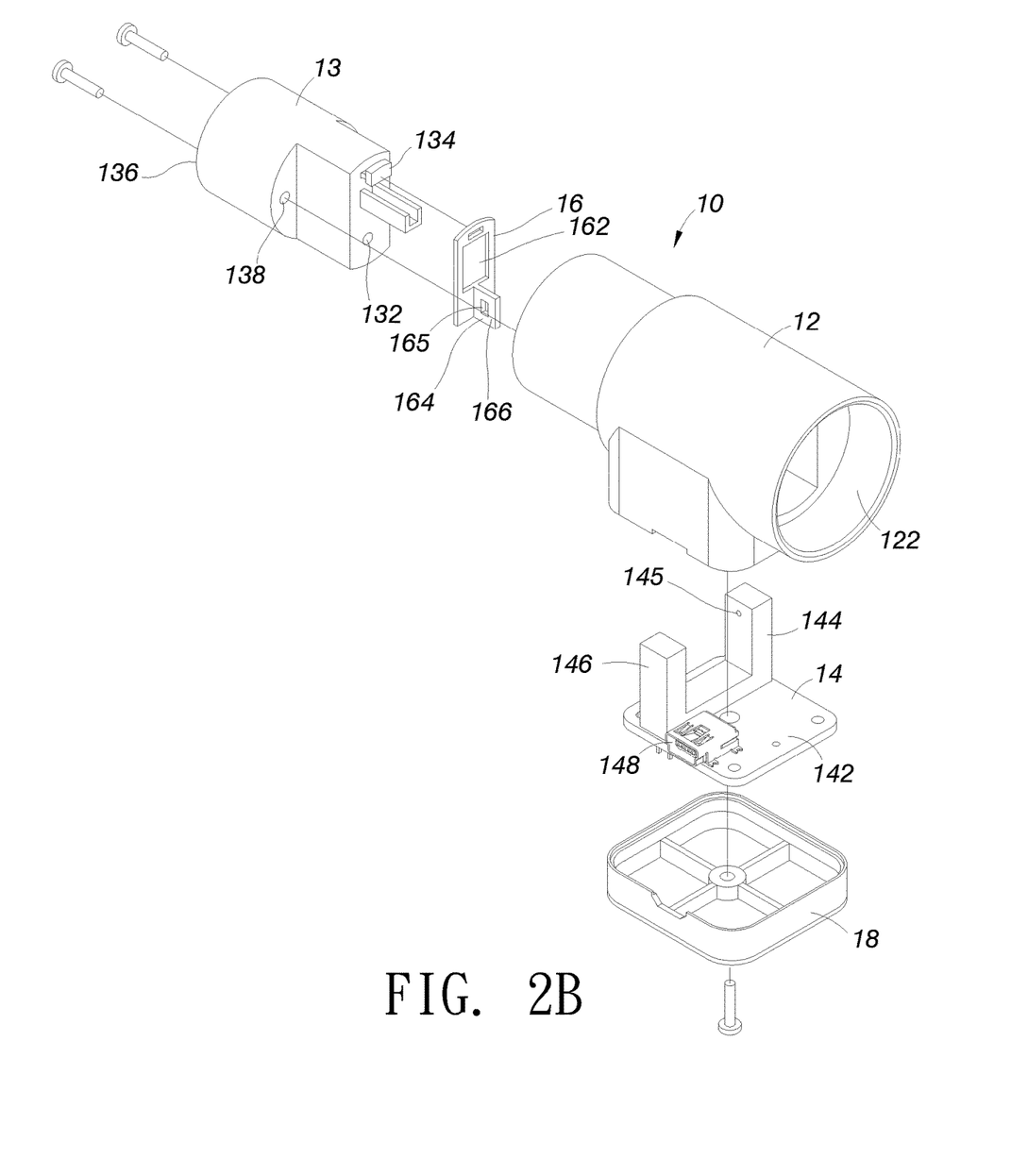
FIG. 2B is an exploded view of a breathing airflow detecting device quency of the patient and the frequency that the nebulizing device supplies medicines is also avoided.
Figure 3A:
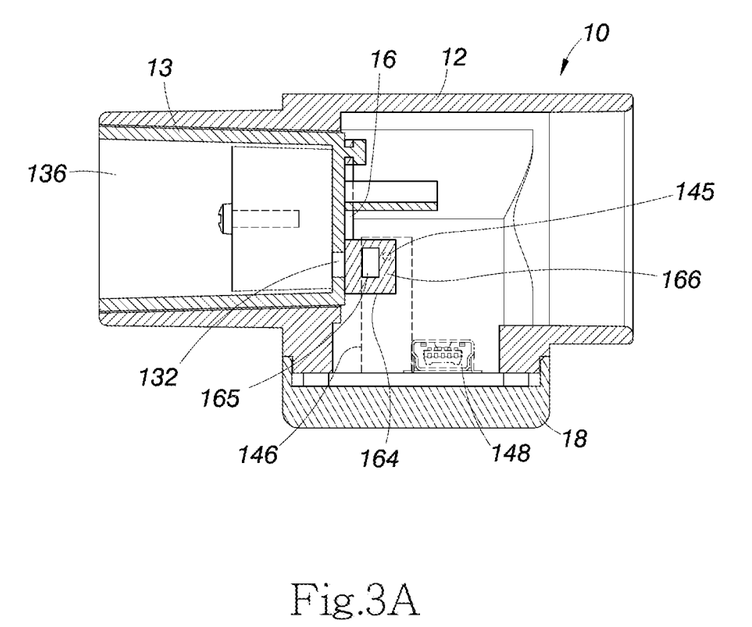
Figure 3B:
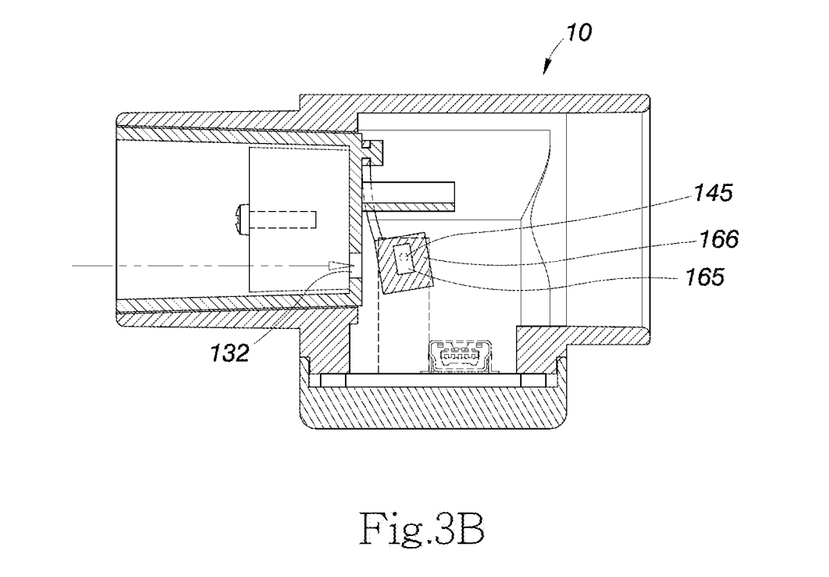
Figure 3C:
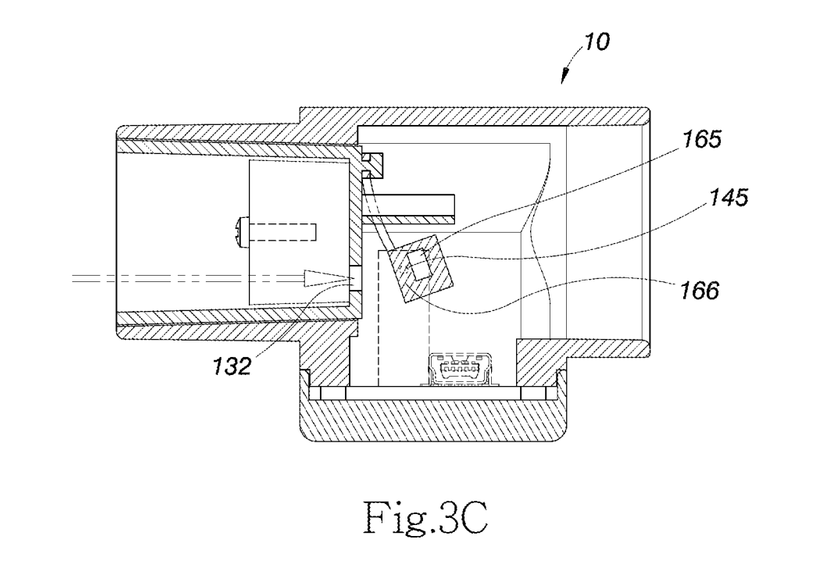
Figure 4:
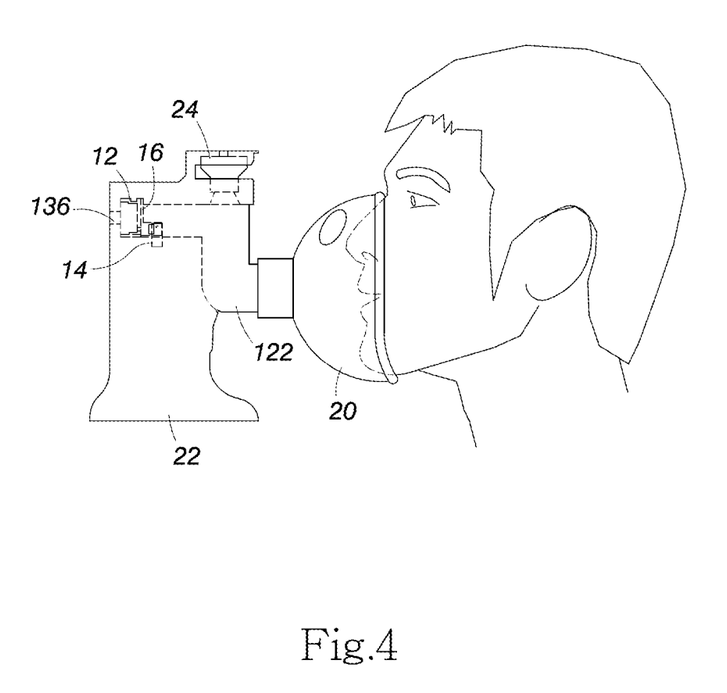
FIG. 4 is a diagram schematically illustrating a breathing airflow det the inlet, the first case is provided with the outlet opposite to the inlet, and the airflow flows into the second case and out of the outlet through the inlet, the second case, and the first case.
Figure 5:
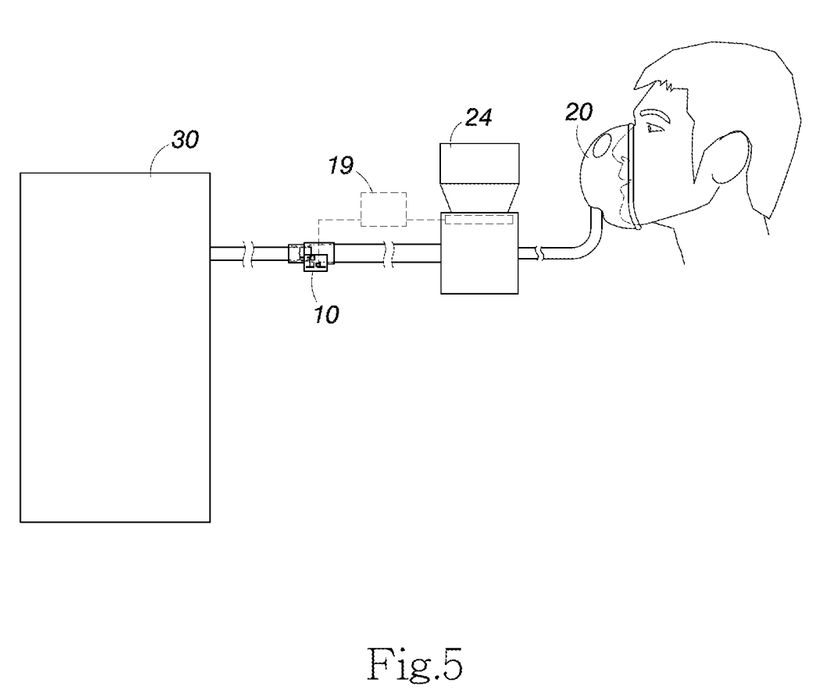
Figure 6:
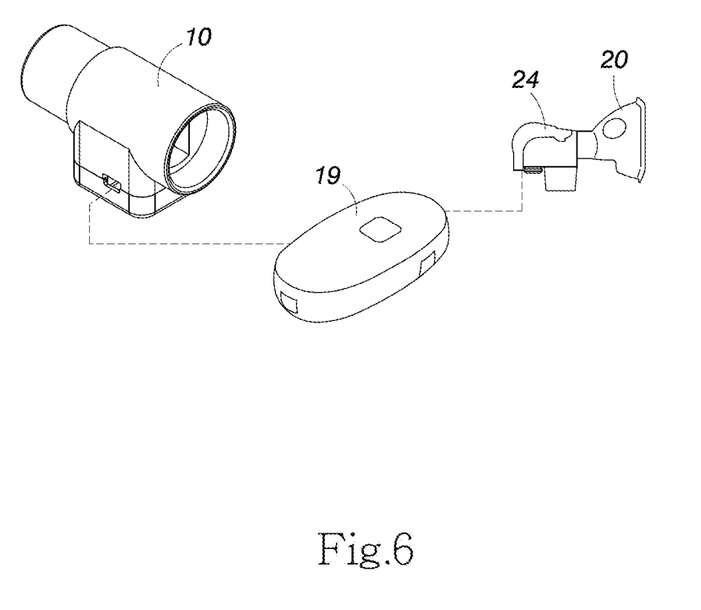
Figure 7A:
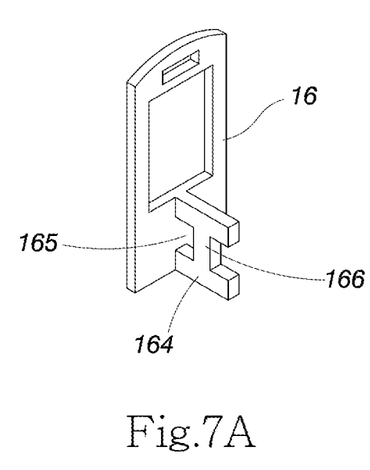
Figure 7B:
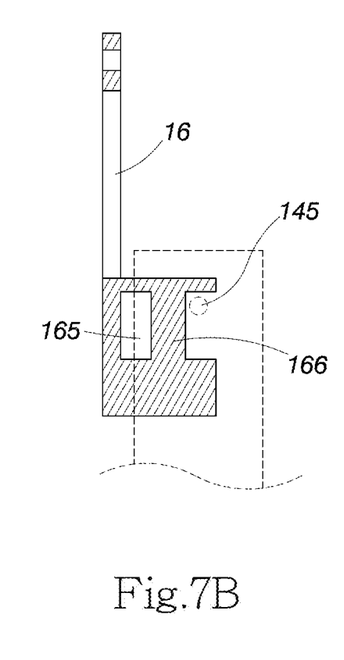
Figure 7C:
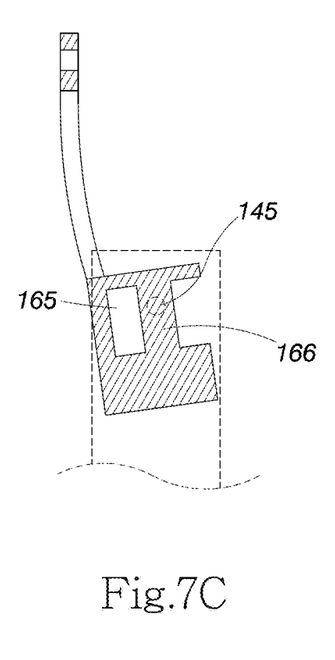
Figure 7D:
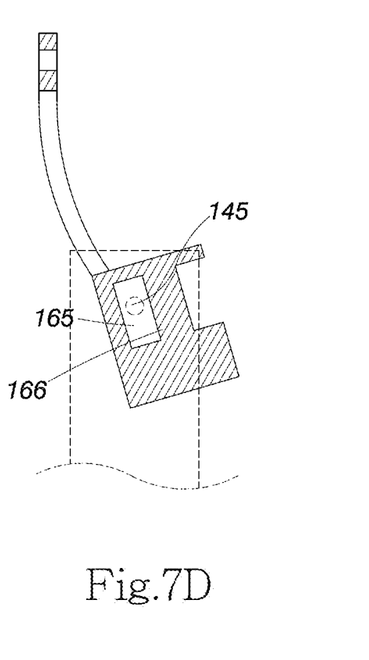

3. The breathing airflow detecting device for a nebulizing device of claim 2, wherein the second case is provided with a vent, and the airflow coming from the inlet passes through the vent and blows the light blocking element.

4. The breathing airflow detecting device for a nebulizing device of claim 1, wherein the light blocking element is penetrated with an opening.

5. The breathing airflow detecting device for a nebulizing device of claim 1, wherein the blocking sheet comprises silicone, plastic, or metal.

6. The breathing airflow detecting device for a nebulizing device of claim 1, wherein the light blocking element is a flexible blocking sheet.

7. The breathing airflow detecting device for a nebulizing device of claim 1, wherein the light emitting element, the light receiving element, and the output port are arranged on a bottom board, and the bottom board is arranged on a bottom base.

8. The breathing airflow detecting device for a nebulizing device of claim 1, wherein the inlet of the at least one case is connected to a mask for receiving breathing airflow exhaled by a user.

* * * * *